United States Patent [19]

Okada et al.

[11] Patent Number: 6,114,524
[45] Date of Patent: Sep. 5, 2000

[54] PROCESS FOR PRODUCING HALOGENATED HETEROARYL COMPOUNDS

[75] Inventors: Shigemitsu Okada; Ryosuke Ushijima, both of Okazaki; Kiyofumi Ishikawa, Saitama, all of Japan

[73] Assignee: Banyu Pharmaceutical Co., Ltd., Tokyo, Japan

[21] Appl. No.: 09/319,642

[22] PCT Filed: Dec. 9, 1997

[86] PCT No.: PCT/JP97/04508

§ 371 Date: Jun. 8, 1999

§ 102(e) Date: Jun. 8, 1999

[87] PCT Pub. No.: WO98/25906

PCT Pub. Date: Jun. 18, 1998

[30] Foreign Application Priority Data

Dec. 10, 1996 [JP] Japan ................................. 8-346666

[51] Int. Cl.$^7$ ....................... C07D 213/02; C07D 215/18; C07D 215/20; C07D 237/12; C07D 237/14

[52] U.S. Cl. .......................... 544/182; 544/183; 544/217; 544/218; 544/235; 544/240; 544/241; 544/253; 544/313; 544/315; 544/319; 544/353; 544/408; 546/290; 546/345

[58] Field of Search ..................... 544/182, 183, 544/240, 235, 241, 313, 315, 319, 353, 408, 253, 217, 218; 546/345, 290

[56] References Cited

U.S. PATENT DOCUMENTS

| | | |
|---|---|---|
| 4,404,388 | 9/1983 | Fäh et al. ................................ 546/345 |
| 4,739,057 | 4/1988 | Leoney-Bay ............................ 544/334 |

FOREIGN PATENT DOCUMENTS

| | | |
|---|---|---|
| 072777 | 8/1982 | European Pat. Off. . |
| 0 155 911 | 9/1985 | European Pat. Off. . |
| 0251246 | 6/1987 | European Pat. Off. . |

OTHER PUBLICATIONS

Paquette In Encyclopedia of Reagents for Organic Synthesis. Vol. 6, p. 4127–4129, 1995.

Journal of Heterocyclic Chemistry: J.B. Paine, "A Conversion of Nicotinate Esters from 3–Cyanopyridones". Vol. 24, No. 2, p. 351 (references cited in the description. particularly p. 351).

*Primary Examiner*—Richard L. Raymond
*Assistant Examiner*—Venkataraman Balasubramanian
*Attorney, Agent, or Firm*—Ladas & Parry

[57] ABSTRACT

The present invention relates to a process for producing a compound represented by the formula (II):

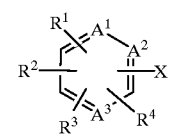

wherein X is a halogen atom, each of $A^1$, $A^2$ and $A^3$ are the same or different and are selected from a carbon atom or a nitrogen atom, provided that at least $A^1$, $A^2$, or $A^3$ is a nitrogen atom. Each of $R^1$, $R^2$, $R^3$ and $R^4$ are the same or different and are selected from a hydrogen atom, a lower alkyl group, a cyano group, a carboxyl group, a lower alkoxycarbonyl group, a halogen atom, and a nitro group. It is also provided that where $R^1$ and $R^2$ are adjacent to each other, $R^1$ and $R^2$ may be combined with each other to form a 5- or 6-membered ring which may carry on the ring thereof one substituent selected from the group consisting of a lower alkyl group, a nitrile group, a carboxyl group, a lower alkoxycarbonyl group, a carbamoyl group, a halogen atom, a nitro group, and an amino-(lower alkyl) group. The compound is prepared by reacting a compound represented by the formula (I):

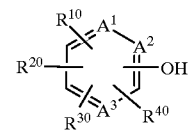

with a quaternary ammonium halide in the presence of phosphorus pentoxide.

4 Claims, No Drawings

PROCESS FOR PRODUCING HALOGENATED HETEROARYL COMPOUNDS

This application is a 371 of PCT/JP97/04508.

TECHNICAL FIELD

The present invention relates to an industrially advantageous process for producing halogenated heteroaryl compounds useful in the chemical industries especially in the field of pharmaceuticals.

BACKGROUND ART

Heretofore, halogenated heteroaryl compounds have been produced by reacting hydroxyheteroaryl compounds with thionyl halides, phosphorus oxyhalides, phosphorus trihalides or phosphorus pentahalides. These prior processes of production, however, require so severe conditions as industrially undesirable. For instance, John B. Pain III [J. Heterocyclic Chem., Vol. 24, Page 351 (1987)] and others produced halogenated heteroaryl compounds by adding a hydroxyheteroaryl compound to boiling phosphorus tribromide (bp. 173° C.). However, it is difficult to control the reaction because this reaction causes a violent generation of heat. In addition, water must be added for the sake of post treatment after the reaction has been completed, which is accompanied by a generation of heat and a large quantity of hydrogen bromide. Further, the phosphorus compounds are in danger of spontaneous ignition. For these reasons, this process is undesirable as an industrial process. Thus, it has been desired to develop a process for producing halogenated heteroaryl compounds under mild conditions.

It is an object of the present invention to develop a process by which halogenated heteroaryl compounds can be produced under mild conditions.

DISCLOSURE OF INVENTION

With the aim of solving the problems mentioned above, the present inventors conducted extensive studies to find a process for producing halogenated heteroaryl compound which comprises reacting a hydroxyheteroaryl compound with a quaternary ammonium halide in the presence of phosphorus pentoxide. Based on this finding, the present invention has been accomplished.

Thus, the present invention relates to a process for producing a compound represented by the following general formula [II]:

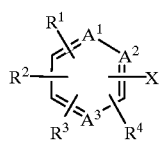

[II]

wherein X is a halogen atom, each of $A^1$, $A^2$ and $A^3$ may be identical or different, is a carbon atom or a nitrogen atom, provided that at least one of $A^1$, $A^2$ and $A^3$ is a nitrogen atom, and each of $R^1$, $R^2$, $R^3$ and $R^4$ may be identical or different, is a hydrogen atom, a lower alkyl group, a cyano group, a carboxyl group, a lower alkoxycarbonyl group, a carbamoyl group, a halogen atom, a nitro group, a hydroxyl group or an amino-(lower alkyl) group, provided that in cases where $R^1$ and $R^2$ are adjacent to each other, $R^1$ and $R^2$ may be combined with each other to form a 5- or 6-membered ring which may carry on the ring thereof one substituent selected from the group consisting of a lower alkyl group, a nitrile group, a carboxyl group, a lower alkoxycarbonyl group, a carbamoyl group, a halogen atom, a nitro group, a hydroxyl group and an amino-(lower alkyl) group; comprises reacting a compound represented by the following general formula [I]:

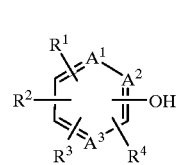

[I]

wherein $A^1$, $A^2$, $A^3$, $R^1$, $R^2$, $R^3$ and $R^4$ are as defined above, with a quaternary ammonium halide in the presence of phosphorus pentoxide.

Next, meanings of the technical terms used in the present specification are explained below.

As used in the present specification, the term "lower alkyl group" means a branched or straight-chain alkyl group having 1 to 6 carbon atoms, of which examples include a methyl group, an ethyl group, a n-propyl group, an isopropyl group, a n-butyl group, an isobutyl group, a tert-butyl group, a n-pentyl group, an isopentyl group, a n-hexyl group, an isohexyl group or the like.

The term "lower alkoxycarbonyl group" means an alkoxycarbonyl group having 1 to 7 carbon atoms, of which examples include a methoxycarbonyl group, an ethoxycarbonyl group, a n-propoxycarbonyl group, an isopropoxycarbonyl group, a n-butoxycarbonyl group, an isobutoxycarbonyl group, a tert-butoxycarbonyl group, a n-pentyloxycarbonyl group, an isopentyloxycarbonyl group, a n-hexyloxycarbonyl group, an isohexyloxycarbonyl group or the like.

The term "aralkyl group" means an aralkyl group having 7 to 13 carbon atoms, of which examples include a benzyl group, a phenethyl group, a phenylpropyl group, a naphthylmethyl group, a naphthylethyl group or the like.

The term "halogen atom" means a fluorine atom, a chlorine atom, a bromine atom or an iodine atom.

The term "amino-(lower alkyl) group" means an amino-substituted, branched or straight-chain alkyl group having 1 to 6 carbon atoms, of which examples include an aminomethyl group, a 2-aminoethyl group, a 1-aminoethyl group, a 2-aminopropyl group, a 3-aminopropyl group, a 4-aminobutyl group, a 5-aminopentyl group, a 6-aminohexyl group or the like.

The term "quaternary ammonium halide" means a quaternary ammonium halide having on the nitrogen atom thereof four substituents which may be identical or different, are selected from the group consisting of the above-defined lower alkyl groups and the above-defined aralkyl groups, wherein the term "aralkyl group" means an aralkyl group having 7 to 12 carbon atoms. Specific examples of said quaternary ammonium halide include tetramethylammonium chloride, tetraethylammonium chloride, tetrapropylammonium chloride, tetrabutylammonium chloride, tetramethylammonium bromide, tetraethylammonium bromide, tetrapropylammonium bromide, tetrabutylammonium bromide, tetramethylammonium iodide, tetraethylammonium iodide, benzyltrimethylammonium chloride, benzyltriethylammonium chloride or the like.

Each of $A^1$, $A^2$ and $A^3$ may be identical or different, is a carbon atom or a nitrogen atom, provided that at least one of $A^1$, $A^2$ and $A^3$ is a nitrogen atom.

Each of $R^1$, $R^2$, $R^3$ and $R^4$ may be identical or different, is a hydrogen atom, a lower alkyl group, a cyano group, a carboxyl group, a lower alkoxycarbonyl group, a carbamoyl group, a halogen atom, a nitro group, a hydroxyl group or an amino-(lower alkyl) group, provided that when $R^1$ and $R^2$ are adjacent to each other, $R^1$ and $R^2$ may be combined with each other to form a 5- or 6-membered ring which may carry on the ring thereof one substituent selected from the group consisting of a lower alkyl group, a nitrile group, a carboxyl group, a lower alkoxycarbonyl group, a carbamoyl group, a halogen atom, a nitro group, a hydroxyl group and an amino-(lower alkyl) group.

The heteroaryl ring represented by the general formula [I] or [II] means a monocyclic heteroaryl ring containing at least one nitrogen atom or, in cases where $R^1$ and $R^2$ in the general formulas are combined with each other to form a 5- or 6-membered ring, a bicyclic heteroaryl ring, such as a pyridine ring, a pyrimidine ring, a pyridazine ring, a quinoline ring, an isoquinoline ring, a quinoxaline ring or the like.

Preferable specific examples of the compound represented by the general formula [I] include 2-hydroxypyridine, kynurenic acid, 3-cyano-6-methyl-2(1H)-pyridinone, 6-butyl-3-cyano-2(1H)-pyridinone, 3-cyano-5-methyl-6-propyl-2(1H)-pyridinone, 2-hydroxyquinoxaline, chelidamic acid or the like.

Next, the process for the production according to the present invention is explained below in more detail.

The halogenated heteroaryl compound [II] of the present invention can be produced by reacting a compound represented by the following general formula [I]:

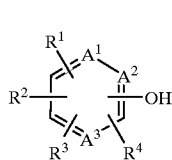

[I]

wherein each of $A^1$, $A^2$ and $A^3$ may be identical or different, is a carbon atom or a nitrogen atom, provided that at least one of $A^1$, A and $A^3$ is a nitrogen atom, and each of $R^1$, $R^2$, $R^3$ and $R^4$ may be identical or different, is a hydrogen atom, a lower alkyl group, a cyano group, a carboxyl group, a lower alkoxycarbonyl group, a carbamoyl group, a halogen atom, a nitro group, a hydroxyl group or an amino-(lower alkyl) group, provided that in cases where $R^1$ and $R^2$ are adjacent to each other, $R^1$ and $R^2$ may be combined with each other to form a 5- or 6-membered ring which may carry on the ring thereof one substituent selected from the group consisting of a lower alkyl group, a nitrile group, a carboxyl group, a lower alkoxycarbonyl group, a carbamoyl group, a halogen atom, a nitro group, a hydroxyl group and an amino-(lower alkyl) group, with a quaternary ammonium halide in the presence of phosphorus pentoxide.

Although the reaction of the compound represented by the general formula [I] and a quaternary ammonium halide in the presence of phosphorus pentoxide may be carried out in the absence of solvent, the reaction is usually carried out in a solvent exercising no adverse influence upon the reaction. The solvents which can preferably be used in this reaction are toluene, chlorobenzene, dichlorobenzene or the like, for instance. The reaction temperature is usually 50° C. or above, and preferably 50° C. to 170° C. Although the reaction time is usually from 30 minutes to 24 hours, a reaction time longer or shorter than the above-mentioned reaction time range may also be adopted, if necessary. Although the quantity of phosphorus pentoxide is appropriately selected in accordance with the kind of the hydroxyheteroaryl compound represented by the general formula [I], it is usually 1 to 5 equivalents and preferably 1 to 2 equivalent per equivalent of the hydroxyheteroaryl compound, and the quantity of the ammonium halide is usually 1 to 5 equivalents and preferably 1 equivalent per equivalent of the hydroxyheteroaryl compound.

After the reaction has been completed, the halogenated heteroaryl compound represented by the general formula [II] can be isolated and purified by known means such as solvent extraction, recrystallization, distillation, various chromatographic treatments, etc.

BEST MODE FOR CARRYING OUT THE INVENTION

Next, the present invention is explained more concretely by referring to the following examples. The invention is by no means limited by these examples.

EXAMPLE 1

Production of 2-bromo-3-cyano-6-methylpyridine

At room temperature, 2.47 g (17 mmol) of phosphorus pentoxide, 2.81 g (8.75 mmol) of tetra-n-butylammonium bromide and 920 mg (7.0 mmol) of 3-cyano-6-methyl-2 (1H)-pyridinone were added to 40 ml of toluene. Then, the mixture thus obtained was heated at 100° C. for one hour with stirring. After washing the toluene layer successively with a saturated aqueous solution of sodium hydrogen carbonate, water and a saturated aqueous solution of sodium chloride, the toluene layer was dried over anhydrous sodium sulfate, and the solvent was distilled off therefrom under a reduced pressure. Thus, 1.00 g (5.07 mmol) of 2-bromo-3-cyano-6-methylpyridine was obtained (yield 72.5%).

EXAMPLES 2–8

The compounds of Examples 2 to 8 can be produced in the same manner as in Example 1.

Table 1 lists the starting materials, reaction conditions, products and yields in Examples 1 to 8. Table 2 summarizes the NMR data and IR data of the products obtained in Examples 1 to 8.

TABLE 1

| Example No. | Starting material | Solvent | Temperature (°C.) | Time (hr) | Product | Yield (%) |
|---|---|---|---|---|---|---|
| 1 | 6-methyl-2-hydroxy-3-cyanopyridine | Toluene | 100 | 1 | 6-methyl-2-bromo-3-cyanopyridine | 72.5 |
| 2 | 6-butyl-2-hydroxy-3-cyanopyridine | Toluene | 100 | 1 | 6-butyl-2-bromo-3-cyanopyridine | 70–90 |
| 3 | 5-methyl-6-propyl-2-hydroxy-3-cyanopyridine | Toluene | 100 | 1 | 5-methyl-6-propyl-2-bromo-3-cyanopyridine | 91 |
| 4 | 2-hydroxyquinoxaline | Toluene | 100 | 2.5 | 2-bromoquinoxaline | 79 |
| 5 | 4-hydroxyquinoline-2-carboxylic acid | Toluene | 100 | 1.5 | 4-bromoquinoline-2-carboxylic acid | 58 |
| 6 | 4-hydroxy-2,6-pyridinedicarboxylic acid | Toluene | 100 | 1 | 4-bromo-2,6-pyridinedicarboxylic acid | 70–80 |
| 7 | 6-butyl-2-hydroxy-3-cyanopyridine | Chlorobenzene | 125 | 3 | 6-butyl-2-chloro-3-cyanopyridine | 82 |
| 8 | 2-hydroxypyridine | 1,2-Dichlorobenzene | 180 | 10 | 2-bromopyridine | 75 |

TABLE 2

| Compound of: | $^1$H-NMR (CDCl$_3$, δ ppm) | IR(KBr, cm$^{-1}$) |
|---|---|---|
| Example 1 | 2.63(3H, s), 7.25(1H, d, J = 8.0 Hz), 7.82(1H, d, J = 8.0 Hz) | 2230, 1580, 1440 |
| Example 2 | 0.94(3H, t, J = 7.3 Hz), 1.38(2H, m), 1.70(2H, m), 2.83(2H) t, J = 7.9 Hz), 7.22(1H, d, J = 7.9 Hz), 7.81(1H, d, J = 7.9 Hz) | 2230, 1580 |
| Example 3 | 1.00(3H, t, J = 7.3 Hz), 1.62(2H, m), 2.59(3H, s), 2.58(2H, m), 7.62(1H, s) | 2240, 1580, 1540, 1420 |
| Example 4 | 7.75–7.95(2H, m), 8.00–8.18(2H, m), 8.87(1H, s) | 1535 |
| Example 5 | 7.75–7.95(2H, m), 8.00–8.18(2H, m), 8.87(1H, m) | 1710, 1550, 1460 |
| Example 6 | 8.37(2H, s) (Solvent: DMSO-d$_6$, his sample only) | 3095, 1734, 1313, 1174, 899 |
| Example 7 | 0.95(3H, t, J = 7.6 Hz), 1.38(2H, m), 1.71(2H, m), 2.84(2H, t, J = 7.9 Hz), 7.20(1H, d, J = 7.9 Hz), 7.88(1H, d, J = 7.9 Hz) | 2230 |
| Example 8 | 7.20–7.30(1H, m), 7.40–7.60(2H, m), 8.38(1H, m) | — |

INDUSTRIAL APPLICABILITY

According to the present invention, halogenated heteroaryl compounds can be produced from hydroxyheteroaryl compounds as starting materials in a high efficiency under mild conditions, and therefore the process of the present invention is useful as an industrial process in high safety.

What is claimed is:

1. A process for producing a compound represented by formula (II):

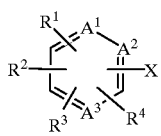

wherein X is a halogen atom, each of $A^1$, $A^2$ and $A^3$ are the same or different, and are selected from a carbon atom or a nitrogen atom, provided that at least one of $A^1$, $A^2$ and $A^3$ is a nitrogen atom, each of $R^1$, $R^2$, $R^3$ and $R^4$ are the same or different, and are selected from the group consisting of a hydrogen atom, a lower alkyl group, a cyano group, a carboxyl group, a lower alkoxycarbonyl group, a halogen atom, and a nitro group, provided that where $R^1$ and $R^2$ are adjacent to each other, $R^1$ and $R^2$ may be combined with each other to form a 5- or 6-membered ring which may carry on the ring thereof one substituent selected from the group consisting of a lower alkyl group, a nitrile group, a carboxyl group, a lower alkoxycarbonyl group, a carbamoyl group, a halogen atom, and a nitro group which comprises reacting a compound represented by the formula (I):

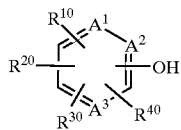

wherein each of $R^{10}$, $R^{20}$, $R^{30}$ and $R^{40}$ may be the same or different, and are selected from a hydrogen atom, a lower alkyl group, a cyano group, a carboxyl group, a lower alkoxycarbonyl group, a carbamoyl group, a halogen atom, a nitro group, provided that in cases where $R^{10}$ and $R^{20}$ are adjacent to each other, $R^{10}$ and $R^{20}$ may be combined with each other to form a 5- or 6-membered ring which may carry on the ring thereof one substituent selected from the group consisting of a lower alkyl group, a nitrile group, a carboxyl group, a lower alkoxycarbonyl group, a carbamoyl group, a halogen atom, a nitro group and $A^1$, $A^2$ and $A^3$ are as defined above, with a quaternary ammonium halide in the presence of phosphorus pentoxide.

2. The process according to claim 1, wherein each of $A^1$ and $A^2$ is a carbon atom, $A^3$ is a nitrogen atom, $R^4$ is hydrogen atom or a lower alkyl group, and each of $R^2$, $R^3$ and $R^4$ are the same or different, and are selected from a hydrogen atom, a lower alkyl group, a nitrile group or a carboxyl group.

3. The process according to claim 1, wherein $A^1$ is a carbon atom or a nitrogen atom, $A^2$ is a carbon atom, $A^3$ is a nitrogen atom, $R^1$ and $R^2$ are combined with each other and form a 6-membered ring which may carry on the ring thereof one substituent selected from the group consisting of a lower alkyl group, a nitrile group and a carboxyl group, and each of $R^3$ and $R^4$ is a hydrogen atom, a lower alkyl group, a nitrile group or a carboxyl group.

4. The process according to claim 1, wherein the compound represented by the formula (I)

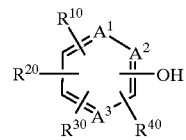

is a quinoline derivative or a quinoxaline derivative wherein $R^{10}$ and $R^{20}$ are combined with each other to form an aromatic 6-membered ring together with the ring of

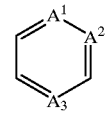

wherein $A^1$, $A^2$ and $A^3$ are as defined in claim 1.

* * * * *